United States Patent [19]

Scherowsky et al.

[11] Patent Number: 4,988,459
[45] Date of Patent: Jan. 29, 1991

[54] USE OF OPTICALLY ACTIVE OXIRANE-2-CARBOXYLIC ACID ESTERS AS DOPANTS IN LIQUID-CRYSTAL MIXTURES, LIQUID-CRYSTAL MIXTURES CONTAINING SAME AND NOVEL OPTICALLY ACTIVE OXIRANE-2-CARBOXYLIC ACID ESTERS

[75] Inventors: Günter Scherowsky; Jürgen Gay, both of Berlin; Hans-Rolf Dübal, Königstein/Taunus; Claus Escher, Mühltal; Wolfgang Hemmerling, Sulzbach; Ingrid Müller, Hofheim am Taunus; Dieter Ohlendorf, Liederbach; Rainer Wingen, Hattersheim am Main, all of Fed. Rep. of Germany

[73] Assignee: Hoechst Aktiengesellschaft, Frankfurt am Main, Fed. Rep. of Germany

[21] Appl. No.: 199,101

[22] Filed: May 26, 1988

[30] Foreign Application Priority Data

May 29, 1987 [DE] Fed. Rep. of Germany ....... 3718174

[51] Int. Cl.$^5$ .............................................. C09K 19/34
[52] U.S. Cl. .......................... 252/299.61; 252/299.01; 350/350 S; 544/238; 544/318; 544/298; 544/335; 546/268; 549/21; 549/22; 549/370; 549/549; 549/512
[58] Field of Search ...................... 252/299.01, 299.61; 350/350 R, 350 S; 544/238, 318, 298, 335; 546/268; 549/21, 22, 370, 549, 512

[56] References Cited

U.S. PATENT DOCUMENTS

| 4,592,858 | 6/1986 | Higuchi et al. | 252/299.66 |
| 4,638,073 | 1/1987 | Walba et al. | 252/299.61 |
| 4,705,874 | 10/1987 | Walba et al. | 252/299.61 |
| 4,789,751 | 12/1988 | Walba et al. | 549/560 |
| 4,835,295 | 5/1989 | Walba et al. | 549/557 |
| 4,876,028 | 10/1989 | Hemmerling et al. | 252/299.61 |
| 4,880,561 | 10/1989 | Tabohashi et al. | 252/299.61 |

FOREIGN PATENT DOCUMENTS

| 244129 | 11/1987 | European Pat. Off. | 252/299.01 |
| 307880 | 3/1989 | European Pat. Off. | 252/299.61 |
| 318423 | 5/1989 | European Pat. Off. | 252/299.61 |
| 3731619 | 4/1988 | Fed. Rep. of Germany | 252/299.01 |
| 63-261230 | 10/1988 | Japan | 252/299.01 |

OTHER PUBLICATIONS

Duebal et al., Jpn. J. Appl. Phys. Part 2, 27(12) L2241, 1988.

Primary Examiner—John S. Maples
Assistant Examiner—Richard Treanor
Attorney, Agent, or Firm—Curtis, Morris & Safford

[57] ABSTRACT

Optically active oxirane-2-carboxylic acid esters with a mesogenic molecular component suitable as dopants in liquid-crystal mixtures. They result in liquid-crystalline ferroelectric phases with short switching times and in electroclinic phases with large electroclinic coefficients. A further advantage lies in the fact that they induce a helix with a very small pitch so that they are also suitable for helix compensation in LC mixtures.

6 Claims, No Drawings

USE OF OPTICALLY ACTIVE OXIRANE-2-CARBOXYLIC ACID ESTERS AS DOPANTS IN LIQUID-CRYSTAL MIXTURES, LIQUID-CRYSTAL MIXTURES CONTAINING SAME AND NOVEL OPTICALLY ACTIVE OXIRANE-2-CARBOXYLIC ACID ESTERS

In the last decade in particular, liquid-crystals have found their way into various technical fields in which electrooptical and display-device properties are required (e.g. in clock, pocket calculator and typewriter displays). These display devices are based on the dielectric alignment effect in the nematic, cholesteric and/or smectic phases of the liquid-crystalline compounds, the molecular longitudinal axis of the compounds taking up—owing to the dielectrical anisotropy—a preferred alignment in an applied electric field. On the other hand, the usual switching times in these display devices are too long for many other potential fields of application of liquid crystals, which are per se very promising chemical compounds for engineering owing to their unique properties. This disadvantage reveals itself, in particular, if a large number of image points have to be driven, as a result of which the production costs of pieces of equipment which contain large surfaces, e.g. video recorders, oscillographs or television, radar, EDP or text-processing display screens, become too high.

In addition to the nematic and cholesteric liquid crystals, optically active smectic liquid-crystal phases have also been acquiring importance to an increasing extent for a few years.

Clark and Lagerwall were able to show that the use of ferroelectric liquid-crystal systems in very thin cells results in electrooptical switching and display elements which have switching times which are faster by a factor of up to 1,000 compared with the conventional TN ("twisted nematic") cells (cf. e.g. Lagerwall et al. "Ferroelectric Liquid Crystals for Displays", SID Symposium, October Meeting 1985, San Diego, Calif., USA). Owing to these and other favorable properties, e.g. The bistable switching facility and the contrast, which is almost independent of viewing angle, FLCs are in principle well suited to the abovementioned fields of application, e.g. via a matrix drive.

Another electrooptical effect, which is described as the electroclinic effect, is exhibited by orthogonal chiral smectic phases, e.g. $S_A^*$, $S_B^*$, $S_E^*$. This effect [S. Garoff and R. B. Meyer, Phys. Rev. Lett. 38, 848 (1977)] consists in a field-induced tilting of the molecules, whose angle of tilt θ varies proportionately to the applied field. The molecules of the orthogonal phases are therefore able to follow the change in field continuously, and they are able, in particular, to follow an alternating field up to a cut-off frequency $f_G$, while ferroelectric systems in each case change their angle of tilt discontinuously on reaching a particular field strength and retain until a suitable field of opposite sign is applied (bistable switching).

Both effects, the ferroelectric and the electroclinic, can be exploited in accordance with their specific properties for constructing electrooptical switching and display elements. For this purpose, either compounds which form tilted or orthogonal smectic phases and are themselves optically active are required or ferroelectric or electroclinic smectic phases can be induced by the doping of compounds, which, although they form such smectic phases, are not themselves optically active, with optically active compounds. The desired phase should at the same time be stable over as large a temperature range as possible.

To achieve a good contrast ratio in electrooptical components, a uniform planar orientation of the liquid crystals is necessary. A good orientation can be achieved in the $S_A^*$ and $S_C^*$ phase if the phase sequence of the liquid-crystal mixture with decreasing temperature is:

Isotrope →N*→$S_A^*$→$S_C^*$. 

The prerequisite is that the pitch (pitch of the helix)in the N* phase is very large (greater than 10 μm) or still better, is completely cancelled out (T. Matsumoto et al., pp 468–470, Proc. of the 6th Int. Display Research Conf., Japan Display, Sept. 30–Oct. 2, 1986, Tokyo, Japan; M. Murakami et al., ibid. p. 344–p. 347). This is achieved by adding to the chiral liquid-crystal mixture, which has e.g. a counter clockwise helix in the N* phase, a further optically active dopant which induces a clockwise helix, in such quantities that the helix is precisely cancelled out.

It has now been found that optically active oxirane-2-carboxylic acid esters result as dopants in short switching times in tilted smectic liquid-crystal phases even with small admixed quantities and in high electro-clinic coefficients in orthogonal smectic liquid-crystal phases. At the same time, it is particularly surprising that the pitch of the helix induced by the doping in the N* phase is so small that even minute admixtures to a twisted phase with oppositely directed sense of rotation can cancel out the twist thereof.

The subject of the invention is therefore the use of optically active oxirane-2-carboxylic acid esters as dopants in liquid-crystal systems. The subject of the invention is furthermore liquid-crystal systems which contain optically active oxirane-2-carboxylic acid esters and also novel optically active oxirane-2-carboxylic acid esters. The oxirane-2-carboxylic acid esters to be used according to the invention correspond to the general formula (I)

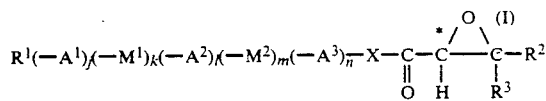

in which the symbols and indices have the following meaning:

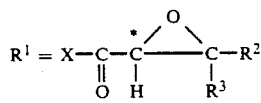

or a straight-chain or branched alkyl radical containing 1 to 16 carbon atoms or a straight-chain or branched alkenyl radical containing 3 to 16 carbon atoms, it being possible for said radicals themselves to contain asymmetric carbon atoms, it being possible for one or more nonadjacent —CH₂— groups to be replaced by —O—, —S—, —CO—, —O—CO— and/or —CO—O—, and it being possible for one or more hydrogen atoms to be replaced by F, Cl, Br or CN, R² = H or alkyl containing 1 to 16 carbon atoms, or cyclohexyl or bicyclohexyl which may also be substituted in each case in position 4 or 4' by an alkyl chain containing 1 to 16 carbon atoms, R³=hydrogen or alkyl containing 1 to 16 carbon atoms, j and l=zero, 1 or 2, k and m=zero or 1, n=zero, 1 or 2, with the following proviso: if j and/or l=zero, k=zero; if n=zero, m=zero; the sum of j+l+n is minimally 1 and maximally 3,

—A¹, —A²=

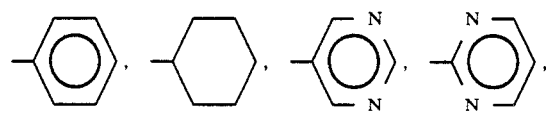

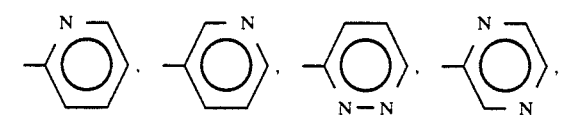

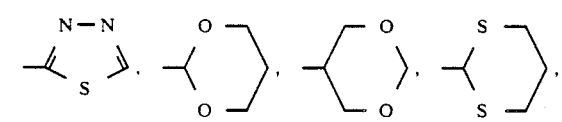

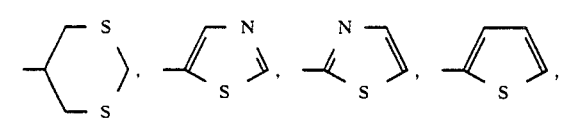

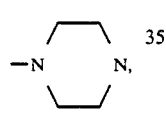

—A³ =

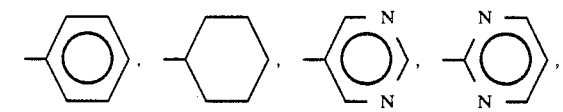

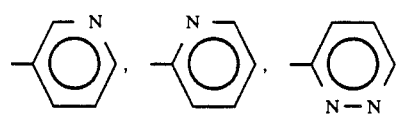

—M¹, —M²=—CO—O, —O—CO, —CH₂CH₂, —CH=CH, —CH₂O, —OCH₂,

X=O or S.

In a preferred embodiment, the symbols in the general formula (I) have the following meaning:

R¹=a straight-chain or branched alkyl or alkenyl radical containing 4 to 14 carbon atoms which may contain an asymmetric carbon atom, or it being possible for a —CH₂-group to be replaced by —O—, —CO— or —CO—O—, or it being possible for one or more H to be replaced by F, R³=H or alkyl containing 1 to 10 carbon atoms, j and l=zero or 1, k, m, n=zero or 1.

In a further preferred embodiment, oxirane-2-carboxylic acid esters of the general formula (IV) are used

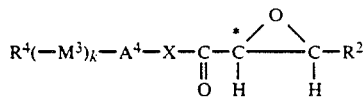

where:

R⁴ denotes a straight-chain or branched alkyl or alkenyl radical containing 6 to 12 carbon atoms which may contain an asymmetric carbon atoms, —M³ denotes —O—, —S—, —O—CO or —CO, —A⁴ denotes

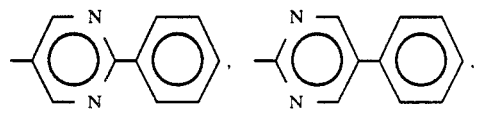

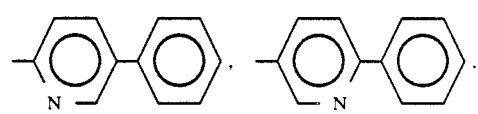

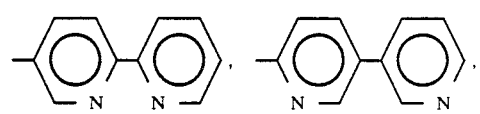

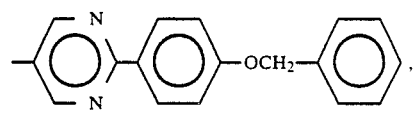

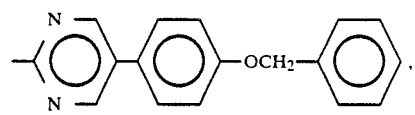

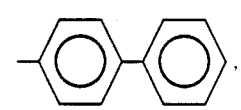

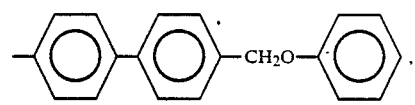

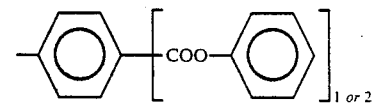

In a particularly preferred embodiment, the radical R² in the general formula (IV) is not equal to H, so that the second carbon atom in the oxirane ring is also chiral. The novel compounds of the general formula (I), in particular (IV), preferably include the compounds mentioned by name in the examples.

To prepare the compounds of the general formula (I), mesogenic phenols or thiophenols of the general formula (II)

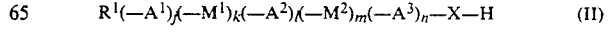

are reacted with derivatives of oxirane-2-carboxylic acid of the formula (III)

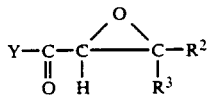

(III)

where Y denotes an OH group or halogen. For Y=OH, the esterification with (II) is carried out in the presence of Brönstedt or Lewis acids, optionally in the presence of hydrophilic agents, or with condensation reagents such as N,N'-carbonyldiimidazole, dicyclohexylcarbodiimide or azodicarboxylic acid esters/triphenylphosphine. For Y=halogen, the reaction with (II) is carried out in the presence of acid scavengers, in particular pyridine or triethylamine. Finally, the alkali-metal or alkaline-earth salts of (II) can also be reacted with the acid halides [(III), Y=halogen] to form (I). The reaction product may be purified by measures known per se, e.g. recrystallization or chromatographic separation processes.

Phenolic or thiophenolic substances of the formula (II) are known. The methods for preparing the derivatives of oxirane-2-carboxylic acid (III) are likewise known, e.g. Sharpless et al., J. Org. Chem. 46, 3936 (1981); Djerassi et al., J. Am. Chem. Soc. 105, 2408 (1983).

The liquid-crystal mixtures according to the invention form liquid-crystal phases and contain at least one optically active oxirane-2-carboxylic acid ester.

The term "liquid-crystal phase" is to be understood to mean nematic, cholesteric, orthogonally smectic or tilted smectic phases, in particular $S_A^*$, $S_B^*$ and $S_C^*$ phases. The liquid-crystal mixtures are composed of 2 to 20, preferably 2 to 15 components, including at least one of the chiral compounds claimed according to the invention.

The other constituents are preferably selected from the known compounds with nematic, cholesteric and/or smectic, e.g. $S_A$, phases, and/or tilted smectic phases; these include, for example, Schiff's bases, biphenyls, terphenyls, phenylcyclohexanes, cyclohexylbiphenyls, heterocyclics containing N, S or O (e.g. pyrimidines), cinnamic acid esters, cholesterol esters, variously bridged, terminal polar polynuclear esters of p-alkylbenzoic acids. In general, the commercially available liquid-crystal mixtures exist, even before the addition of the optically active compound(s), as mixtures of very varied components, at least one of which is mesogenic, i.e. exhibits a liquid-crystal phase as a compound, in the form of a derivative or mixed with certain co-components, which permits at least one enantiotropic (clearing point>melting point) or monotropic (clearing point<melting point) mesophase formation to be anticipated. In particular, the liquid-crystal mixture contains, in addition to at least one of the optically active compounds claimed according to the invention, an ester compound with $S_c$ phase, e.g. a phenyl ester of an alkoxybenzoic acid, or a biaromatic compound with a nitrogen-containing heterocyclic, e.g. an alkylpyrimidinylalkoxybenzene.

The liquid-crystal mixtures in general contain 0.05 to 70% by weight, in particular 0.1 to 50% by weight, of the compound or compounds according to the invention. The compounds according to the invention are suitable, in particular, as dopants for tilted smectic liquid-crystal phases since they convert the latter into ferroelectric liquid-crystal phases; the values for the spontaneous polarization ($P_s$) are, with a doping level of 10 mol-%, and at 25° C. in the range of about 1–15 $nC/cm^2$ and in the range of about 10–150 $nC/cm^2$ linearly extrapolated to the pure compound, and some of the values for $P_s$ are even higher.

The switching times of the novel systems are frequently below 100 μs for a doping level of 10 mol-%, 25° C. and a switching voltage of ±10 V/μm. Particularly outstanding is the result of the Substance Example 7 which has the R,R configuration and has the highest spontaneous polarization and also the shortest switching time (see Table 1, Application Example A9). The compounds according to the invention may also be used to achieve the electroclinic effect in orthogonal smectic phases ($S_A^*$, $S_B^*$, $S_E^*$).

EXAMPLE 1

4-(2-n-octylthiopyrimidin-5-yl)phenyl (2R,3S)-3-nonyloxirane-2-carboxylate

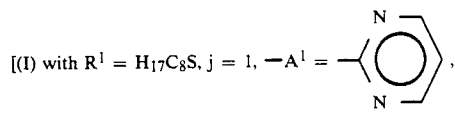

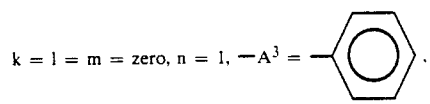

$X = O, R^2 = C_9H_{19}, R^3 = H$]

A solution of 413 mg (2.0 mmol) of dicyclohexyldicarbodiimide in 10 ml of dry $CH_2Cl_2$ is added while stirring at room temperature to 429 mg (2 mmol) of (2R,3S)-3-nonyloxirane-2-carboxylic acid, 633 mg (2 mmol) of 4-(2-n-octylthiopyrimidin-5-yl) phenol and also 20 mg of 4-dimethylaminopyridine. After stirring for 4 hours at room temperature, the reaction solution is evaporated down in vacuo. After chromatographic purification and recrystallization from n-hexane, 120 mg (12%) of colorless crystals are obtained. The substance exhibits the liquid-crystal phase sequence: X 73 $S_A$ 93.5 I.

The following are obtained analogously:

EXAMPLE 2

4-(2-n-octylthiopyrimidin-5-yl)phenyl (2R,3S)-3-pentyloxirane-2-carboxylate

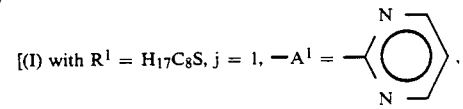

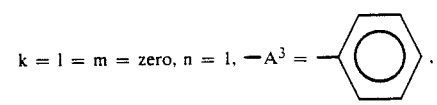

$X = O, R^2 = C_5H_{11}, R^3 = H$]

Phase sequence: X 61.4 $S_A$ 84.5 I

EXAMPLE 3

4-(2-n-octyloxypyrimidin-5-yl)phenyl (2R,3S)-3-pentyloxirane-2-carboxylate

[(l) with $R^1 = H_{17}C_8O$, j = 1, $-A^1 =$ 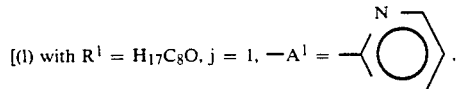, k = l = m = zero, n = 1, $-A^3 =$ 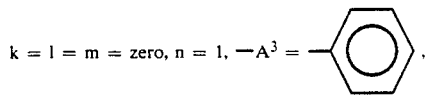,

X = O, $R^2 = C_5H_{11}$, $R^3 = H$]

Phase sequence: X 47.5 $S_2$ 75.6 $S_1$ 115.8 I

EXAMPLE 4

4-(2-n-octyloxypyrimidin-5-yl)phenyl (2R,3S)-3-nonyloxirane-2-carboxylate

[(l) with $R^1 = H_{17}C_8O$, j = 1, $-A^1 =$ 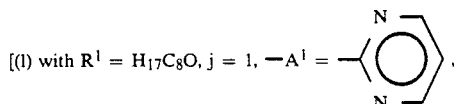, k = l = m = zero, n = 1, $-A^3 =$ 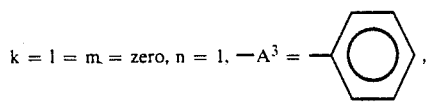,

X = O, $R^2 = C_9H_{19}$, $R^3 = H$]

Phase sequence: X 55 $S_3$ 59 $S_2$ 93 $S_A$ 118 I

EXAMPLE 5

4-(2-n-octylpyrimidin-5-yl)phenyl (2R,3S)-3-nonyloxirane-2-carboxylate

[(l) with $R^1 = H_{17}C_8$, j = 1, $-A^1 =$ 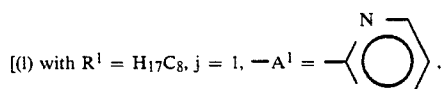, k = l = m = zero, n = 1, $-A^3 =$ 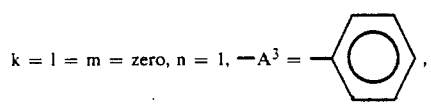,

X = O, $R^2 = C_9H_{19}$, $R^3 = H$]

Phase sequence: X 48 $S_2$ 99 $S_A$ 105 I

EXAMPLE 6

4-(2-n-octylpyrimidin-5-yl)phenyl (2R,3S)-3-propyloxirane-2-carboxylate

[(l) with $R^1 = H_{17}C_8$, j = 1, $-A^1 =$ 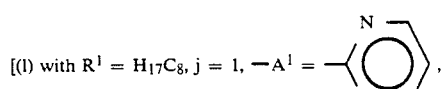, k = l = m = zero, n = 1, $-A^3 =$ 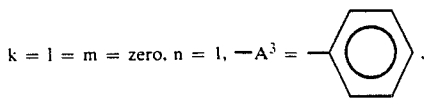,

X = O, $R^2 = C_3H_7$, $R^3 = H$]

Phase sequence: X 66 $S_A$ 86 I

EXAMPLE 7

4-(2-n-octylpyrimdin-5-yl)phenyl (2R,3R)-3-methyloxirane-2-carboxylate

[(l) with $R^1 = H_{17}C_8$, j = 1, $-A^1 =$ 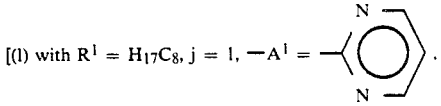, k = l = m = zero, n = 1, $-A^3 =$ 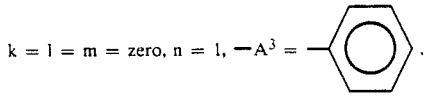,

X = O, $R^2 = CH_3$, $R^3 = H$]

Melting point: 77° C.

EXAMPLE 8

4-(5-n-nonylpyrimidin-2-yl)phenyl (2R,3S)-3-octyloxirane-2-carboxylate

[(l) with $R^1 = H_{19}C_9$, j = 1, $-A^1 =$ 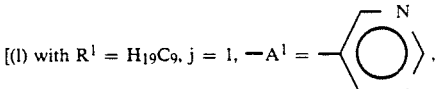, k = l = m = zero, n = 1, $-A^3 =$ 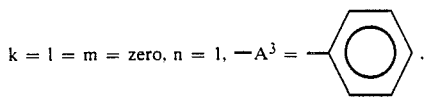,

X = O, $R^2 = C_8H_{17}$, $R^3 = H$]

Phase sequence: X 53 $S_A$ 63 N* 64 I

EXAMPLE 9

4-(5-n-octylpyrimidin-2-yl)phenyl (2R,3S)-3-propyloxirane-2-carboxylate

[(l) with $R^1 = H_{17}C_8$, j = 1, $-A^1 =$ 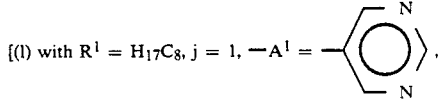, k = l = m = zero, n = 1, $-A^3 =$ 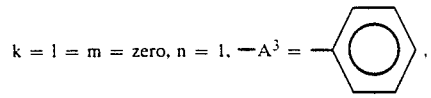,

X = O, $R^2 = C_3H_7$, $R^3 = H$]

Melting point: 62° C.

EXAMPLE 10

4-(5-n-octylpyrimidin-2-yl)phenyl (2R,3R)-3-methyloxirane-2-carboxylate

[(I) with $R^1 = H_{17}C_8$, j = 1, $-A^1 =$ 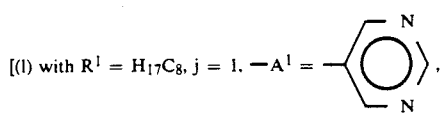, k = l = m = zero, n = 1, $-A^3 =$ 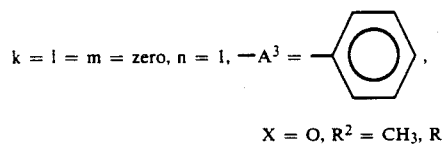

X = O, $R^2 = CH_3$, $R^3 = H$]

Melting point: 67° C.

EXAMPLE 11

4-Decyloxyphenyl (2R,3S)-3-[trans-4-(trans-4-heptylcyclohexyl)cyclohexyl]oxirane-2-carboxylate

[(I) with $R^1 = H_{21}C_{10}O$, j = k = l = m = zero, n = 1, $-A^3 =$ 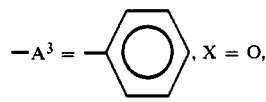, X = O, $R^2 =$ 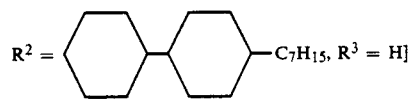 $-C_7H_{15}$, $R^3 = H$]

Phase sequence: X 67.2 $S_B$ 125.9 $S_A$ 164.4 I

EXAMPLE 12

4-Dodecyloxyphenyl (2R,3S)-3-[trans-4-(trans-4-heptylcyclohexyl)cyclohexyl]oxirane-2-carboxylate

[(I) with $R^1 = H_{25}C_{12}O$, j = k = l = m = zero, n = 1, $-A^3 =$ 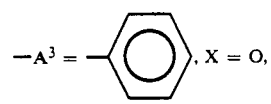, X = O, $R^2 =$ 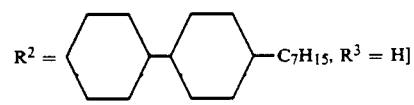 $-C_7H_{15}$, $R^3 = H$]

Phase sequence: X 79 $S_1$ 156 I

EXAMPLE 13

4-Dodecyloxyphenyl (2R,3S)-3-(trans-4-pentyl-cyclohexyl)oxirane-2-carboxylate

[(I) with $R^1 = H_{25}C_{12}O$, j = k = l = m = zero, n = 1, $-A^3 =$ 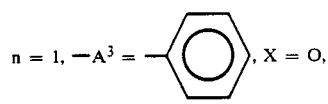, X = O, $R^2 =$ 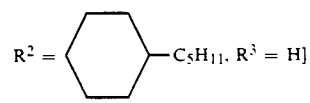 $-C_5H_{11}$, $R^3 = H$]

Melting point: 69° C.

EXAMPLE 14

4'-Octyloxybiphenyl-4-yl (2R,3S)-3-octyloxirane-2-carboxylate

[(I) with $R^1 = H_{17}C_8O$, j = 1, $-A^1 =$ 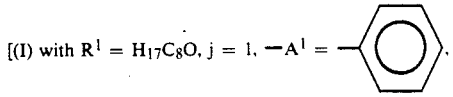, k = l = m = zero, n = 1, $-A^3 =$ 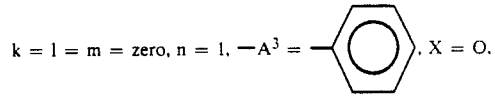, X = O, $R^2 = C_8H_{17}$, $R^3 = H$]

Phase sequence: X 117.5 $S_2$ 118 $S_A$ 119 I

EXAMPLE 15

4-(4-Decyloxybenzoyloxy)phenyl (2R,3S)-3-propyloxirane-2-carboxylate

[(I) with $R^1 = H_{21}C_{10}O$, j = 1, $-A^1 =$ 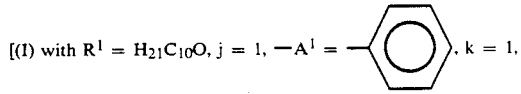, k = 1, $-M^1 = -\overset{\overset{O}{\|}}{C}-O$, l = m = zero, n = 1, $-A^3 =$ 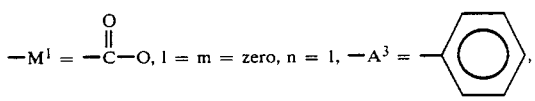,

X = O, $R^2 = C_3H_7$, $R^3 = H$]

Phase sequence: X 82.5 N* 103.5 I

EXAMPLE 16

4-(4-Decyloxybenzoyloxy)biphenyl-4'-yl (2R,3S)-3-octyloxirane-2-carboxylate

[(I) with $R^1 = H_{21}C_{10}O$, j = 1, $-A^1 =$ 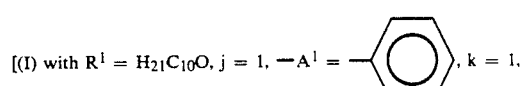, k = 1, $-M^1 = -\overset{\overset{O}{\|}}{C}-O$, l = m = zero, n = 2, $-A^3 =$ 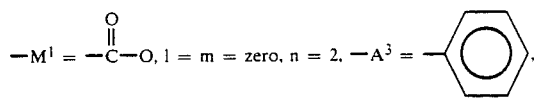,

X = O, $R^2 = C_8H_{17}$, $R^3 = H$]

Phase sequence X 117 $S_2$ 122 $S_C$* 186 N* 200 I

EXAMPLE 17

4-(4'-Octyloxybiphenyl-4-carbonyloxy)phenyl (2R,3S)-3-nonyloxirane-2-carboxylate

[(I) with $R^1 = H_{17}C_8O$, j = 2, $-A^1 =$ 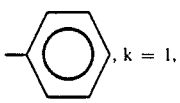, k = 1, $-M^1 = -\overset{O}{\underset{\|}{C}}-O$, l = m = zero, n = 1, $-A^3 =$ 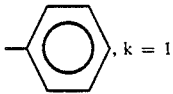,

X = O, $R^2 = C_9H_{19}$, $R^3 = H$]

Melting point: 139° C.

EXAMPLE 18

4-(4-(4-Octyloxybenzoyloxy)benzoyloxy)phenyl (2R,3S)-3-nonyloxirane-2-carboxylate

[(I) with $R^1 = H_{17}C_8O$, j = 1, $-A^1 =$ 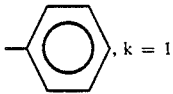, k = 1, $-M^1 = -\overset{O}{\underset{\|}{C}}-O$, l = 1, $-A^2 =$ , m = 1, $-M^2 = -\overset{O}{\underset{\|}{C}}-O$, n = 1, $-A^3 =$  X = O, $R^2 = C_9H_{19}$, $R^3 = H$]

Phase sequence: X 118 $S_C^*$ 167 $S_A^*$ 177 N* 207 I

EXAMPLE 19

4-(4-Octyloxybenzyloxy)phenyl (2R,3S)-3-nonyloxirane-2-carboxylate (I) with $R^1 = H_{17}C_8O$, j = 1, $-A^1 =$ 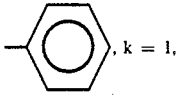, k = 1, $-M^1 = -CH_2O$, l = m = zero, n = 1, $-A^3 =$ 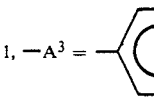,

X = O, $R^2 = C_9H_{19}$, $R^3 = H$]

Melting point: 101° C.

EXAMPLE 20

4-(4'-Octylbiphenyl-4-methyleneoxy)phenyl (2R,3S)-3-nonyloxirane-2-carboxylate

[(I) with $R^1 = H_{17}C_8$, j = 2, $-A^1 =$ 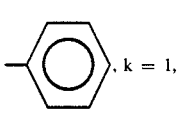, k = 1, $-M^1 = -CH_2O$, l = m = zero, n = 1, $-A^3 =$ ,

X = O, $R^2 = C_9H_{19}$, $R^3 = H$]

Melting point: 164° C.

EXAMPLE 21

4,4'-Biphenyl bis[(2R,3S)-3-nonyloxirane-2-carboxylate]

[(I) with $R^1 = $ (2R, 3S)-3-Nonyl-oxiran-2-carbonyloxy, $R^2 = C_9H_{19}$, $R^3 = H$, j = k = l = m = zero, n = 2, $-A^3 =$ 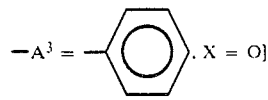, X = O]

Melting point: 158° C.

EXAMPLE 22

4-(4-Decyloxybenzoyloxy)phenyl (2R,3S)-3-nonyloxirane-2-carboxylate

[(I) with $R^1 = H_{21}C_{10}O$, j = 1, $-A^1 =$ 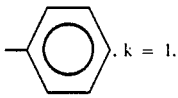, k = 1, $-M^1 = -\overset{O}{\underset{\|}{C}}O$, l = m = zero, n = 1, $-A^3 =$ 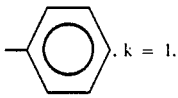,

X = O, $R^3 = C_9H_{19}$, $R^3 = H$]

Phase sequence: X 91 $S_C$ 102 N* 105 I

EXAMPLE 23

4-(2-n-Octylpyrimidin-5-yl)phenyl (2R,3R)-3-propyloxirane-2-carboxylate

[(I) with $R^1 = H_{17}C_8$, j = 1, $-A^1 =$ , k = l = m = zero, n = 1, $-A^3 =$ 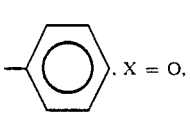, X = O, $R^2 = C_3H_7$, $R^3 = H$]

Melting point: 83° C.

EXAMPLE 24

(5-n-Octylpyrimidin-2-yl)phenyl (2R,3R)-3-propyloxirane-2-carboxylate

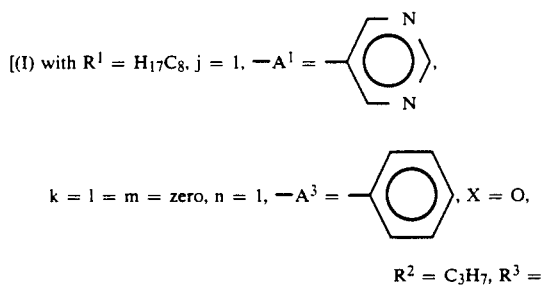

[(I) with $R^1 = H_{17}C_8$, j = 1, $-A^1 =$ pyrimidine, k = l = m = zero, n = 1, $-A^3 =$ phenyl, X = O, $R^2 = C_3H_7$, $R^3 = H$]

Melting point: 40° C.

EXAMPLE 25

4-(2-n-Octylthiopyrimidin-5-yl)phenyl (2R,3R)-3-methyloxirane-2-carboxylate

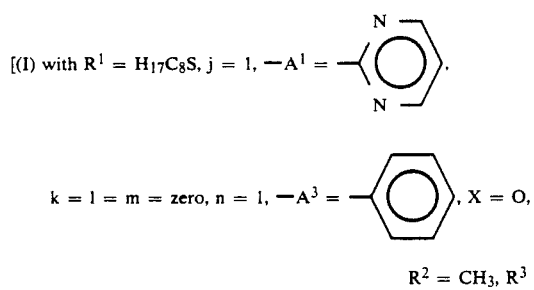

[(I) with $R^1 = H_{17}C_8S$, j = 1, $-A^1 =$ pyrimidine, k = l = m = zero, n = 1, $-A^3 =$ phenyl, X = O, $R^2 = CH_3$, $R^3 = H$]

Melting point: 67° C.

EXAMPLE 26

4-(2-n-Octyloxypyrimidin-5-yl)phenyl (2R,3R)-3-methyloxirane-2-carboxylate

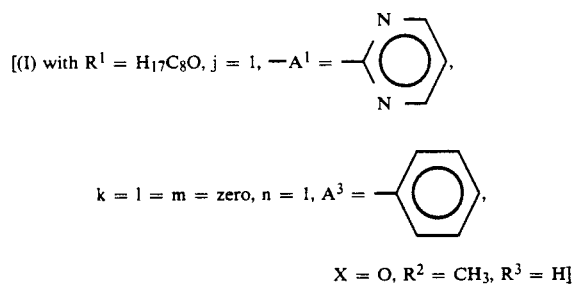

[(I) with $R^1 = H_{17}C_8O$, j = 1, $-A^1 =$ pyrimidine, k = l = m = zero, n = 1, $A^3 =$ phenyl, X = O, $R^2 = CH_3$, $R^3 = H$]

Melting point: 97° C.

EXAMPLE 27

4-(2-((S)-7-Methylnonyloxy)pyrimidin-5-yl)phenyl (2R,3R)-3-methoxyloxirane-2-carboxylate

[(I) with $R^1 = H_5C_2\overset{*}{C}H(CH_3)(-CH_2)_6O$, j = 1,

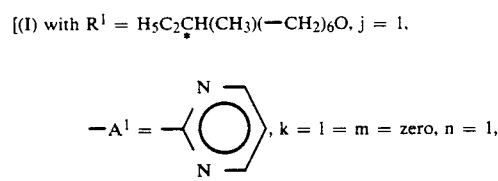

$-A^1 =$ pyrimidine, k = l = m = zero, n = 1,

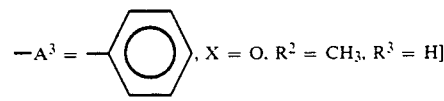

$-A^3 =$ phenyl, X = O, $R^2 = CH_3$, $R^3 = H$]

Melting point: 87° C.

EXAMPLE 28

4-(2-((S)-7-Methylnonyloxy)pyrimidin-5-yl)phenyl (2R,3R)-3-propyloxirane-2-carboxylate

[(I) with $R^1 = H_5C_2\overset{*}{C}H(CH_3)(-CH_2)_6O$, j = 1,

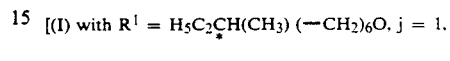

$-A^1 =$ pyrimidine, k = l = m = zero, n = 1,

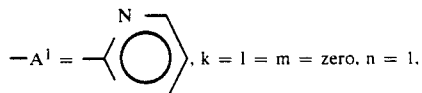

$-A^3 =$ phenyl, X = O, $R^2 = C_3H_7$, $R^3 = H$]

Melting point: 45° C.

EXAMPLE 29

[(4-(2-Octyloxypyrimidin-5-yl)]phenyl (2R,3R)-3-propyloxirane-2-carboxylate

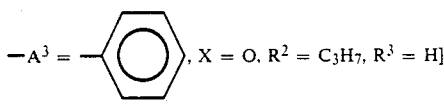

[(I) with $R^1 = H_{17}C_8O$, j = 1, $-A^1 =$ pyrimidine,

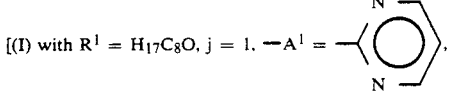

k = l = m = zero, n = 1, $-A^3 =$ phenyl,

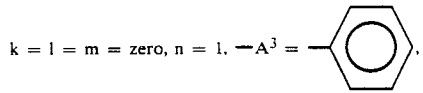

X = O, $R^2 = C_3H_7$, $R^3 = H$]
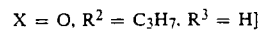

Melting point: 62° C.

EXAMPLE 30

[4-(5-Octyloxypyrimidin-2-yl)]phenyl (2R,3R)-3-propyloxirane-2-carboxylate

[(I) with $R^1 = H_{17}C_8O$, j = 1, $-A^1 =$ pyrimidine,

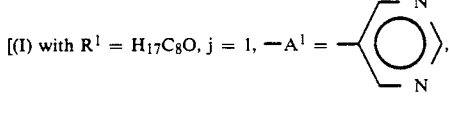

k = l = m = zero, n = 1, $-A^3 =$ phenyl,

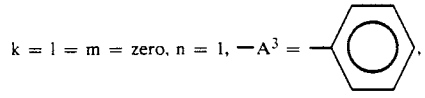

X = O, $R^2 = C_3H_7$, $R^3 = H$]
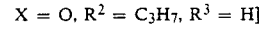

Melting point: 67° C.

EXAMPLE 31

2-(4-Octyloxyphenyl)pyrimidin-5-yl (2R,3R)-3-propyloxirane-2-carboxylate

[(I) with $R^1 = H_{17}C_8O$, j = 1, $-A^1 =$ —⟨phenyl⟩, k = l = m = zero, n = 1, $-A^3 =$ —⟨pyrimidine (N,N)⟩,

X = O, $R^2 = C_3H_7$, $R^3 = H$]

Melting point: 83° C.

EXAMPLE 32

4-(4-Octyloxybenzoyloxy)-biphenyl-4′-yl (2R,3R)-3-propyloxirane-2-carboxylate

[(I) with $R^1 = H_{17}C_8O$, j = k = 1, $A^1 =$ —⟨phenyl⟩, $-M^1 = -CO-O$, l = m = 1, n = 2, $A^3 =$ —⟨phenyl⟩,

X = O, $R^2 = C_3H_7$, $R^3 = H$]

Phase sequence: X ($S_A^*$ 121 N* 123) 131 I

EXAMPLE 33

4-(2-(10-Undecen-1-yl)oxypyrimidin-5-yl)phenyl (2R,3R)-3-propyloxirane-2-carboxylate

[(I) with $R^1 = H_2C = CH(-CH_2)_9O$, j = 1, $-A^1 =$ —⟨pyrimidine (N,N)⟩, k = l = m = zero, n = 1, $-A^3 =$ —⟨phenyl⟩, X = O, $R^2 = C_3H_7$, $R^3 = H$]

Melting point: 61° C.

EXAMPLE 34

4-(2-(1,1-H-Perfluorooctyl)oxypyrimidin-5-yl)phenyl (2R,3R)-3-propyloxirane-2-carboxylate

[(I) with $R^1 = F_{15}C_7CH_2O$, j = 1, $-A^1 =$ —⟨pyrimidine (N,N)⟩, k = l = m = zero, n = 1, $-A^3 =$ —⟨phenyl⟩, X = O, $R^2 = C_3H_7$, $R^3 = H$]

Meltng point: 99° C.

EXAMPLE 35

4-(5-Octyl-1,3-dioxan-2-yl)phenyl (2R,3R)-3-propyloxirane-2-carboxylate

[(I) with $R^1 = H_{17}C_8$, j = 1, $-A^1 =$ —⟨1,3-dioxane⟩, k = l = m = zero, n = 1, $-A^3 =$ —⟨phenyl⟩, X = O, $R^2 = C_3H_7$, $R^3 = H$]

Melting point: 59° C.

EXAMPLE 36

4-(2-Nonyloxypyrimidin-5-yl)phenyl (2R,3R)-3-propyloxirane-2-carboxylate

[(I) with $R^1 = H_{19}C_9O$, j = 1, $-A^1 =$ —⟨pyrimidine (N,N)⟩, k = l = m = zero, n = 1, $-A^3 =$ —⟨phenyl⟩, X = O, $R^2 = C_3H_7$, $R^3 = H$]

Melting point: 68° C.

EXAMPLE 37

4-(2-Decyloxypyrimidin-5-yl)phenyl (2R,3R)-3-propyloxirane-2-carboxylate

[(I) with $R^1 = H_{21}C_{10}O$, j = 1, $-A^1 =$ —⟨pyrimidine (N,N)⟩, k = l = m = zero, n = 1, $-A^3 =$ —⟨phenyl⟩, X = O, $R^2 = C_3H_7$, $R^3 = H$]

Melting point: 70° C.

EXAMPLE 38

4-(5-Octylpyridin-2-yl)phenyl (2R,3R)-3-propyloxirane-2-carboxylate

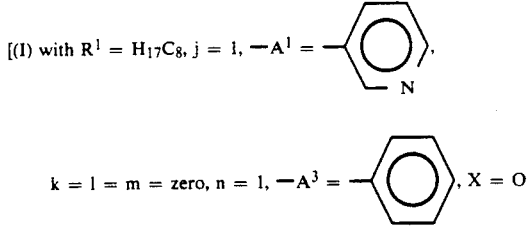

[(I) with $R^1 = H_{17}C_8$, j = 1, $-A^1 =$ pyridyl, k = l = m = zero, n = 1, $-A^3 =$ phenyl, X = O $R^2$ $C_3H_7$, $R^3 =$ H]

Melting point: 53° C.

EXAMPLE 39

2-(4-Pentyloxycarbonylphenyl)-pyrimidin-5-yl (2R,3R)-3-propyloxirane-2-carboxylate

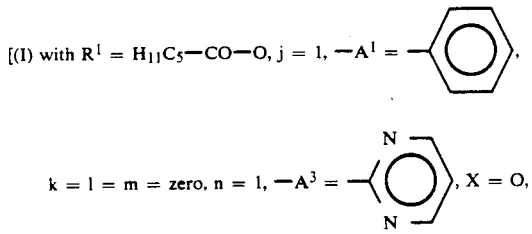

[(I) with $R^1 = H_{11}C_5-CO-O$, j = 1, $-A^1 =$ phenyl, k = l = m = zero, n = 1, $-A^3 =$ pyrimidyl, X = O, $R^2 = C_3H_7$, $R^3 =$ H]

Melting point: 82° C.

EXAMPLE 40

4-(4-Trans-pentylcyclohexyl)phenyl (2R,3R)-3-propyloxirane-2-carboxylate

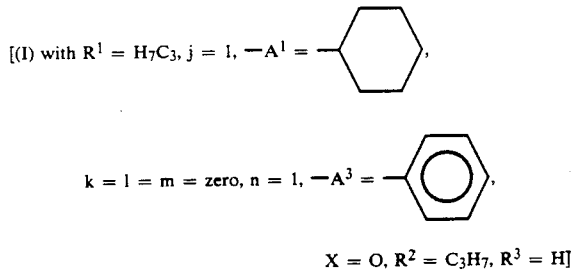

[(I) with $R^1 = H_7C_3$, j = 1, $-A^1 =$ cyclohexyl, k = l = m = zero, n = 1, $-A^3 =$ phenyl,

X = O, $R^2 = C_3H_7$, $R^3 =$ H]

Melting point: 46° C.

EXAMPLE 41

4-(2-(4-Hexyloxyphenyl)pyrimidin-5-yl)phenyl (2R,3R)-3-propyl-oxirane-2-carboxylate

[(I) with $R^1 = H_{13}C_6O$, j = 1 = n = 1, k = m = zero,

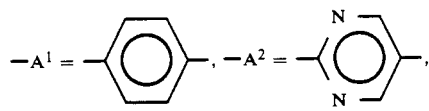

-continued

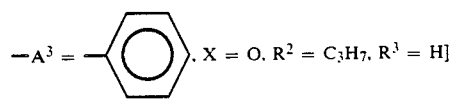

$-A^3 =$ phenyl, X = O, $R^2 = C_3H_7$, $R^3 =$ H]

Phase sequence: X 121 $S_A$ 151 I

EXAMPLE 42

2-(4-(5-Oxohexyl)oxyphenyl)pyrimidin-5-yl)phenyl (2R,3R)-3-propyloxirane-2-carboxylate

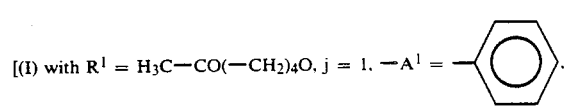

[(I) with $R^1 = H_3C-CO(-CH_2)_4O$, j = 1, $-A^1 =$ phenyl,

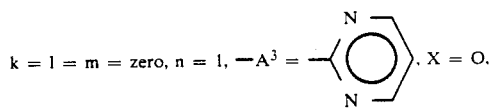

k = l = m = zero, n = 1, $-A^3 =$ pyrimidyl, X = O, $R^2 = C_3H_7$, $R^3 =$ H]

Melting point: 84° C.

EXAMPLE 43

4-(5-Octyl-1,3-dithian-2-yl)phenyl (2R,3R)-3-propyloxirane-2-carboxylate

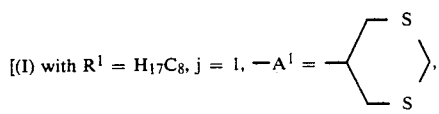

[(I) with $R^1 = H_{17}C_8$, j = 1, $-A^1 =$ dithianyl, k = l = m = zero, n = 1, $-A^3 =$ phenyl, X = O, $R^2 = C_3H_7$, $R^3 =$ H]

Melting point: 102° C.

EXAMPLE 44

2-(4-(4-trans-propylcyclohexyl)carbonyloxyphenyl)-pyrimidin-5-yl (2R,3R)-3-propyloxirane-2-carboxylate

[(I) with $R^1 = H_7C_3$, j = k = l = n = 1, m = zero,

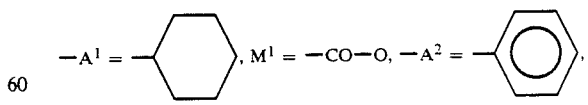

$-A^1 =$ cyclohexyl, $M^1 = -CO-O$, $-A^2 =$ phenyl,

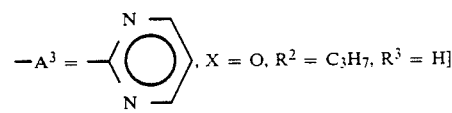

$-A^3 =$ pyrimidyl, X = O, $R^2 = C_3H_7$, $R^3 =$ H]

Melting point: 141° C.

EXAMPLE 45

4-(2-((S)-8-Methyldecyl)pyrimidin-5-yl)phenyl (2R,3R)-3-methyloxirane-2-carboxylate

[(I) with $R^1 = H_5C_2\overset{*}{C}H(CH_3)(-CH_2)_7$, j = 1,

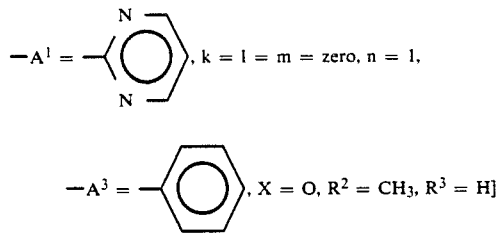

, k = l = m = zero, n = 1,

, X = O, $R^2 = CH_3$, $R^3 = H$]

Melting point: 73° C.

APPLICATION EXAMPLES A1 to A20

To check the effectiveness of the above described compounds as ferroelectric dopants in liquid-crystal systems with tilted smectic phases, they were mixed in concentrations of 10 mol-% in each case with the racemate of the compound

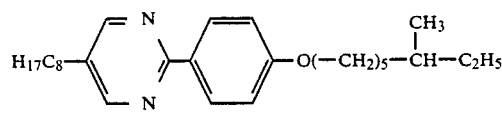  (A)

Phase sequence: K 14.9 $S_c$ 49.8 $S_A$ 59.2 I
(5° C.)

4-(5-Octylpyrimidin-2-yl)-1-(6-methyloctyl-1-oxy)benzene or of the compound

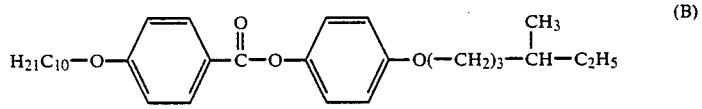  (B)

Phase sequence: K 17 $S_G$ 32.7 $S_c$ 70.4 $S_A$ 73.3 I
(−3° C.)

4-(4-Decyloxyphenyl-1-carbonyloxy)-1-(4-methylhexyloxy)benzene or of a nonchiral basic mixture (C) of the phase sequence

K 13 $S_C$ 51 $S_A$ 62 N 67 I    (C)

or of a further nonchiral basic mixture (D) having the phase sequence

K 12.5 $S_C$ 83 $S_A$ 95 N 100 I    (D)

In each case the values for the spontaneous polarization ($P_s$ in nC.cm$^{-2}$), for the switching time τ(in μs) and for the optical angle of tilt of the $S_c$-phase θ (in °) of the mixture were determined. The $P_s$ values are measured by the method of H. Diamant et al. (Rev. Sci. Instr., 28, 30, 1957), use being made of a special measuring cell [Skarp et al. in Ferroelectric Letters Vol. 06, 67 (1986)] in which the τ and θ values are also determined. With a cell layer thickness of approx. 2 μm a uniform planar orientation of the liquid crystals in the $S_c$ phase is achieved by shearing [SSFLC technique, Clark et al., Appl. Phys. Lett. 36, 899 (1980)]. To determine τ and θ, the measuring cell is mounted on the rotating stage of a polarization microscope between crossed analyzer and polarizer. The optical angle of tilt or switching angle 2θ is determined by rotating the measuring cell from maximum to minimum light transmission. The determination of the switching time τ, is carried out by means of a photo-diode by measuring the rise time of the light signal from 10 to 90% of the signal level. The switching voltage is ±10 V/μm. The $S_c$ range of the respective mixture is specified in addition to the values for $P_s$, τ, 2θ; at the same time, the values in brackets specify the subcoolable lower temperature limit of the $S_c$ range.

Table 1 summarizes the results.

TABLE 1

| Substance example | Application example | Host | Temp. °C. | $S_c$*-range in the mixture in °C. | $P_s$ nC/cm$^2$ | τ μs | 2θ degree |
|---|---|---|---|---|---|---|---|
| 11 | A1 | B | 25 | 34–65 | 6.4 | 76 | 45 |
| 12 | A2 | B | 25 | [35]–65 | 4 | 130 | 44 |
| 13 | A3 | A | 40 | [5]–40 | 2 | 200 | 28 |
| 14 | A4 | A | 40 | 8–50 | 1.3 | 180 | 44 |
| 8 | A5 | A | 40 | 5–46 | 6 | 75 | 38 |
| 15 | A6 | B | 25 | [30]–58 | 11 | 35 | 58 |
| 3 | A7 | C | 25 | 7[5]–40 | 3 | 55 | 35 |
| 2 | A8 | C | 25 | 32–46 | 3.2 | 290 | 38 |
| 7 (R.R) | A9 | C | 25 | 28[20]–44 | 15 | 19 | 36 |
| 24 | A10 | D | 25 | 10–68.5 [−8] | 55.8 | 14/28 | 50/30 |
| 25 | A11 | D | 25 | 10–73.5 | 18.2 | 20/48 | 50/22 |
| 26 | A12 | D | 25 | 14–78 [−5] | 46.4 | 21/57 | 55/13 |
| 27 | A13 | D | 25 | 13–78 | 47 | 26/70 | 52/15 |
| 28 | A14 | D | 25 | 8–77.5 [−6,5] | 63.9 | 21/55 | 59/14 |
| 29 | A15 | D | 25 | 9–77.5 | 62 | 25/62 | 60/21 |

TABLE 1-continued

| Substance example | Application example | Host | Temp. °C. | $S_C^*$-range in the mixture in °C. | $P_s$ nC/cm² | τ μs | 2θ degree |
|---|---|---|---|---|---|---|---|
| 30 | A16 | D | 25 | [−6]<br>9–73 | 45.4 | 25/50 | 52/24 |
| 31 | A17 | D | 40 | [−6]<br>50–73 | 78.3 | 6.6/17.8 | 62/18 |
| 36 | A18 | D | 25 | [+21]<br>10–79 | 63 | 21.5/55 | 57/24 |
| 37 | A19 | D | 25 | [−5]<br>10–79,5 | 70.3 | 15.6/45.4 | 58/21 |
| 45 | A20 | D | 25 | [−4]<br>10–71<br>[−7] | 45.4 | 19/46 | 52/16 |

[ ] The temperatures marked with a bracket are subcooling temperatures

APPLICATION EXAMPLES A21 to A30

In each case one of the compounds according to the invention was added to the nonchiral liquid-crystal mixture C with the phase sequence I→N→$S_A$→$S_C$ and their twisting power (generation of a helix) in the nematic and in the $S_C^*$ phase was investigated. As described e.g. in P. Kassubek et al., Mol. Cryst. Liq. Cryst., Vol. 8, page 305 to 314, 1969, the determination of the pitch of the induced helix was carried out in a wedge cell with an orientation layer by measuring the displacement lines under a polarization microscope. The determination of the pitch in the $S_C^*$ phase was carried out on the basis of the diffraction pattern of a He-Ne laser beam (K. Kondo et al. Jpn. J. Appl. Phys. 21, 224 (1982)) and also by measuring the displacement strips in a polarization microscope. Table 2 summarizes the results.

Particularly striking is the enormous twisting power of the substance of Example 10 (Application Example A21) which is therefore outstandingly suitable for pitch compensation in liquid-crystal mixtures both in the N* and also in the $S_C^*$ phase.

TABLE 2

| Substance example | Application example | Temperature °C. | HTP[(1)] 1/μm | Phase |
|---|---|---|---|---|
| 10 | A21 | 62 | 7.5 | N* |
| 3 | A22 | 25 | 15.1 | $S_C^*$ |
|  |  | 60 | 11.4 | N* |
| 7 | A23 | 25 | 15.6 | $S_C^*$ |
| 26 | A24 | 63 | 8.3 | N* |
| 27 | A25 | 62.5 | 9.5 | N* |
| 28 | A26 | 91.5 | 4.6 | N* |
| 29 | A27 | 91.5 | 5.8 | N* |
| 30 | A28 | 94 | 4.5 | N* |
| 31 | A29 | 89 | 9.1 | N* |
| 36 | A30 | 92 | 5.8 | N* |

[(1)]HTP (helical twisting power) = $(x \cdot p)^{-1}$
x = mole fraction of the dopant in the basic mixture C
p = pitch

APPLICATION EXAMPLE A31

In orthogonal smectic phases ($S_A$, $S_B$, $S_E$), the compounds of the formula (I) induce the electroclinic effect, whose magnitude is specified by the differential coefficient (dθ/dE). θ is the angle of tilt induced by the electric field E. The measurement of this parameter was carried out in the $S_A^*$ phase, but in the same "bookshelf" arrangement and in the same cell which was used also for the polarization measurements (see Application Examples A1 to A20). The angle of tilt induced by the electric field is measured in a polarization microscope with crossed polarizers by locating the dark positions, reading off the associated angle on the rotating stage and subtracting from the latter the angle measured without field. To check the effectiveness of the compounds (I), the electroclinic coefficient of the mixture defined in Application Example A9 was determined at a temperature of 48° C. We obtained (dθ/dE)=2.5 . 10⁻⁹ rad m/V.

We claim:

1. An optically active oxirane-2-carboxylic acid ester of the formula (I)

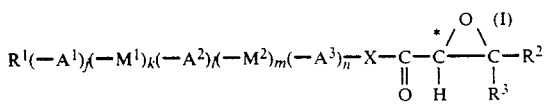

wherein

R¹ is

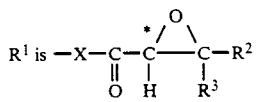

or a straight-chain or branched alkyl radical containing 1 to 16 carbon atoms or a straight-chain or branched alkenyl radical containing 3 to 16 carbon atoms, it being possible for said radicals themselves to contain asymmetric carbon atoms, it being possible for one or more nonadjacent —CH₂— groups to be replaced by —O—, —S—, —CO—, —O—CO— and/or —CO—O—, and it being possible for one or more hydrogen atoms to be replaced by F, Cl, Br or CN;

R² is H or alkyl containing 1 to 16 carbon atoms or cyclohexyl which may be substituted in 4-position by an alkyl chain containing 1 to 16 carbon atoms or 1,1'-bicyclohexyl which may be substituted in 4'-position by an alkyl chain containing 1 to 16 carbon atoms;

R³ is H or alkyl containing 1 to 16 carbon atoms;

X is O or S; and

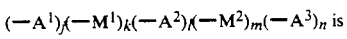

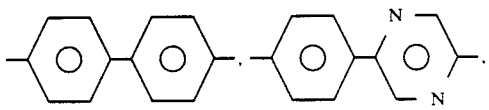

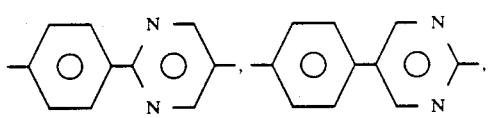

-continued

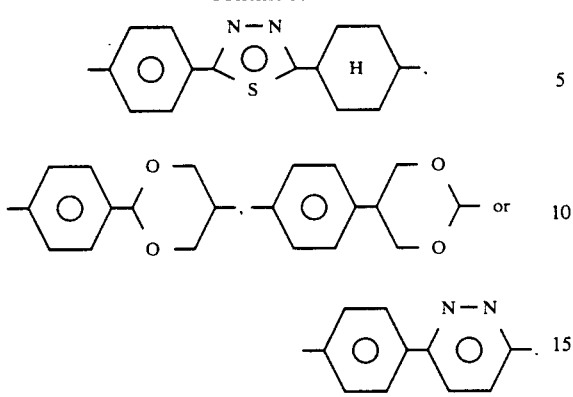

2. An oxirane-2-carboxylic acid ester as claimed in claim 1 having the formula (IV)

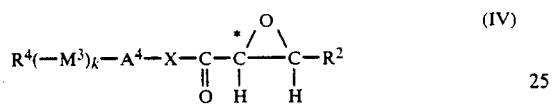

wherein

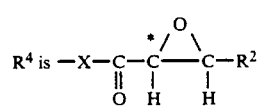

or a straight-chain or branched alkyl radical containing 1 to 16 carbon atoms or a straight-chain or branched alkenyl radical containing 3 to 16 carbon atoms, it being possible for said radicals themselves to contain asymmetric carbon atoms, it being possible for one or more nonadjacent —$CH_2$— groups to be replaced by —O—, —S—, —CO—, —O—CO— and/or —CO—O, and it being possible for one or more hydrogen atoms to be replaced by F, Cl, Br or CN;

$R^2$ is H or alkyl containing 1 to 16 carbon atoms or cyclohexyl which may be substituted in 4-position by an alkyl chain containing 1 to 16 carbon atoms or 1,1'-bicyclohexyl which may be substituted in 4'-position by an alkyl chain containing 1 to 16 carbon atoms;

$M^3$ is —O, —S, —O—CO, or —CO;

k is zero or 1; and $A^4$ is

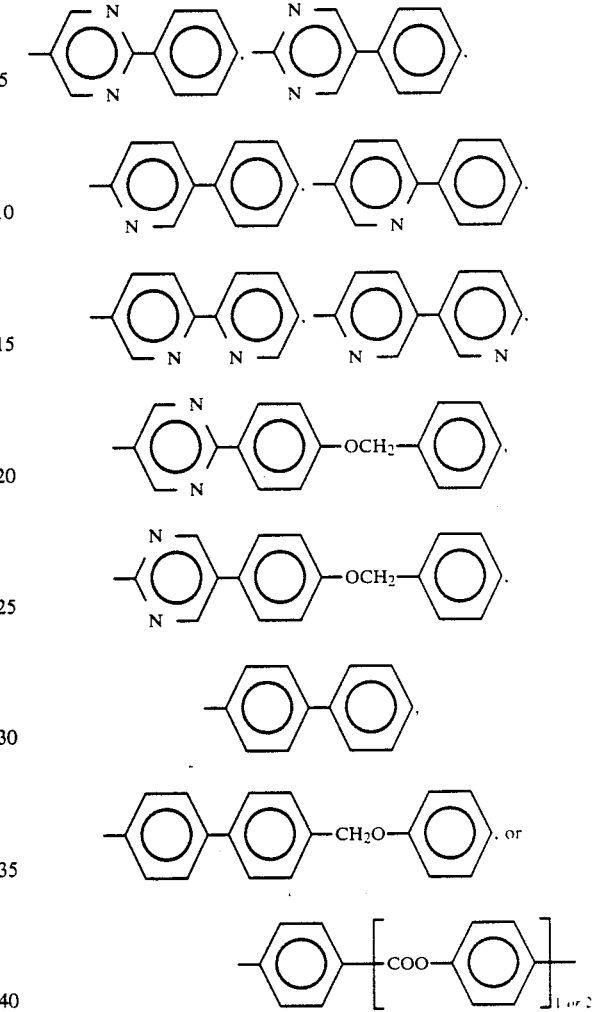

3. An oxirane-2-carboxylic acid ester as claimed in claim 2 wherein $R^4$ is a straight-chain or branched alkyl or alkenyl radical containing 6 to 12 carbon atoms which may contain an asymmetric carbon atom.

4. A liquid-crystal mixture containing at least two components, wherein at least one component is an optically active oxirane-2-carboxylic acid ester of the formula (I) as claimed in claim 1.

5. A liquid-crystal mixture containing at least two components, wherein at least one component is an optically active oxirane-2-carboxylic acid ester of the formula (IV) as claimed in claim 2.

6. An electrooptically switching or display element containing a liquid-crystal mixture as claimed in claim 5.

* * * * *